(12) United States Patent
Terry et al.

(10) Patent No.: US 12,295,811 B2
(45) Date of Patent: May 13, 2025

(54) LIGATURE DEVICE AND METHOD OF USE

(71) Applicant: Chinook Contract Research Inc., Victoria (CA)

(72) Inventors: Richard N. Terry, Conyers, GA (US); Merle E. Olson, Calgary (CA); Nicholas D. Allan, Victoria (CA)

(73) Assignee: Chinook Contract Research Inc. (CA)

( * ) Notice: Subject to any disclaimer, the term of this patent is extended or adjusted under 35 U.S.C. 154(b) by 154 days.

(21) Appl. No.: 17/966,722

(22) Filed: Oct. 14, 2022

(65) Prior Publication Data

US 2023/0104037 A1 Apr. 6, 2023

Related U.S. Application Data

(63) Continuation of application No. 16/638,120, filed as application No. PCT/US2018/046150 on Aug. 9, 2018, now Pat. No. 11,596,510.

(60) Provisional application No. 62/544,662, filed on Aug. 11, 2017.

(51) Int. Cl.
*A61D 7/00* (2006.01)
*A61B 17/00* (2006.01)
*A61B 17/12* (2006.01)
*A61D 1/04* (2006.01)
*A61D 1/06* (2006.01)
*A61K 31/167* (2006.01)

(52) U.S. Cl.
CPC .......... *A61D 7/00* (2013.01); *A61B 17/12009* (2013.01); *A61D 1/04* (2013.01); *A61D 1/06* (2013.01); *A61K 31/167* (2013.01); *A61B 2017/00526* (2013.01); *A61B 2017/00889* (2013.01); *A61B 2017/00893* (2013.01); *A61B 2017/12018* (2013.01)

(58) Field of Classification Search
CPC . A61C 7/303; A61D 7/00; A61D 1/04; A61D 1/06; A61B 17/12; A61B 17/12009; A61B 17/12013; A61B 2017/00526; A61B 2017/00889; A61B 2017/00893; A61B 2017/12018; A61K 31/167; A61L 31/16
See application file for complete search history.

(56) References Cited

U.S. PATENT DOCUMENTS

| 4,195,075 A | 3/1980 | Miller |
| 4,930,451 A | 6/1990 | Miller et al. |
| 5,505,958 A | 4/1996 | Bello et al. |

(Continued)

FOREIGN PATENT DOCUMENTS

ES 2566577 A2 4/2016

OTHER PUBLICATIONS

International Search Report for PCT/US2018/046150 mailed Feb. 14, 2019.

(Continued)

*Primary Examiner* — Robert A Lynch
(74) *Attorney, Agent, or Firm* — Workman Nydegger

(57) ABSTRACT

The present invention is an apparatus and method for ligation of livestock animals. The ligation apparatus or band provides topical active agent(s) that alleviate pain during various ligature procedures. This invention also relates to a method that includes applying a loop or band around a body part for elastomeric ligation, whereby the band material supplies a topical active agent (s) to the body part to reduce the pain of ligation.

14 Claims, 4 Drawing Sheets

(56) References Cited

U.S. PATENT DOCUMENTS

| | | | |
|---|---|---|---|
| 6,001,384 | A | 12/1999 | Jeannin |
| 8,568,426 | B2 | 10/2013 | Straehnz et al. |
| 11,596,510 | B2 | 3/2023 | Terry et al. |
| 2003/0012806 | A1* | 1/2003 | McBride-Sakal .......................... A61B 17/12013 424/423 |
| 2005/0271694 | A1 | 12/2005 | Mansouri |
| 2006/0052757 | A1 | 3/2006 | Fischer |
| 2006/0259041 | A1* | 11/2006 | Hoffman ............ A61B 1/00087 606/139 |
| 2007/0191869 | A1 | 8/2007 | Wadsworth et al. |
| 2010/0233227 | A1* | 9/2010 | Weber ....................... A61P 9/00 623/1.42 |
| 2017/0031916 | A1 | 2/2017 | Smith |
| 2017/0319316 | A1 | 11/2017 | Smith et al. |
| 2020/0246122 | A1 | 8/2020 | Terry et al. |
| 2025/0017714 | A1 | 1/2025 | Allan et al. |

OTHER PUBLICATIONS

Written Opinion for PCT/US2018/046150 mailed Feb. 14, 2019.
Extended European Search Report for EP 18844097.8 mailed Apr. 14, 2021.
J. Crank, The Mathematics of Diffusion, Journal, 1975, 1-421, 2nd Edition, Brunel University, Clarendon Press, Oxford.
Marti et al., Effect of band and knife castration of beef calves on welfare indicators of pain at three relevant industry ages: II. Chronic pain, Journal, 2017, 4367-4380, American Society of Animal Science.
USP Monographs: Lidocaine Hydrochloride and Epinephrine Injection, 2007.
Tanaka et al., Lidocaine Concentration in Oral Tissue by the Addition of Epinephrine, Journal, 2016, Anesth Prog 63:17-24, American Dental Society of Anesthesiology.
Moya et al., Effects of castration method and frequency of intramuscular injections of ketoprofen on behavioral and physiological indicators of pain in beef cattle, Journal, 2014, 92:1684-1695, American Society of Animal Science.
Melendez et al., Effect of band and knife castration of beef calves on welfare indicators of pain at three relevant Industry ages: I. Acute pain, Journal, 2017, 95:4352-4366, American Society of Animal Science.
Advisory Action received for U.S. Appl. No. 16/638,120, mailed on Jul. 6, 2022, 3 pages.
Advisory Action received for U.S. Appl. No. 16/638,120, mailed on May 26, 2022, 3 pages.
Chia et al., "Threshold temperatures and thermal requirements of black soldier fly Hermetia illucens: Implications for mass production", PLOS ONE, 2018, 13(11).
Colvin et al., "Benchmarking Australian sheep parasite control practices: a national online survey", Animal Prod Sci, 2020, 61: 237-245.
Final Office Action received for U.S. Appl. No. 16/638,120, mailed on Apr. 19, 2022, 10 pages.
Florentino et al., "Development and validation of a microbiological assay for determination of chlorhexidine digluconate in aqueous solution", BJPS, 2013, 49(2): 351-358.
Holdsworth et al., "World Association for the Advancement of Veterinary Parasitology (W.A.A.V.P.) guidelines for evaluating the efficacy of ectoparasiticides against myiasis causing parasites on ruminants", Vet Parasitol, 2006, 136 (1): 15-28.
International Preliminary Report on Patentability received for PCT Patent Application No. PCT/US18/46150, mailed on Feb. 20, 2020, 8 pages.
International Search Report and Written Opinion received for PCT Patent Application No. PCT/CA2024/050216, mailed on May 24, 2024, 15 pages.
International Search Report and Written Opinion received for PCT Patent Application No. PCT/US18/46150, mailed on Oct. 15, 2018, 9 pages.
International Search Report for PCT/CA2024/050216 mailed on May 24, 2024.
Kotze et al., "Control of sheep flystrike: what's been tried in the past and where to from here", Aust Vet J, 2022, 100: 1-19.
Kotze et al., "Resistance to dicyclanil and imidacloprid in the sheep blowfly, Lucilia cuprina, in Australia", Pest Manag Sci, 2022, 78: 4195-4206.
Lane et al., "Priority list of endemic diseases for the red meat industries", Project Report BAHE0010 Meat & Livestock Australia Limited, Sydney, 2015: 282.
Levot et al., "), In vitro effectiveness of ivermectin and spinosad flystrike treatments against larvae of the Australian sheep blowfly Lucilia cuprina (Wiedemann) (Diptera: Calliphoridae)", Australian Journal of Entomology, 2008, 47: 365-369.
Non-Final Office Action received for U.S. Appl. No. 16/638,120, mailed on Feb. 4, 2022, 17 pages.
Non-Final Office Action received for U.S. Appl. No. 16/638,120, mailed on Jul. 28, 2022, 12 pages.
Notice of Allowance received for U.S. Appl. No. 16/638,120, mailed on Nov. 2, 2022, 9 pages.
Patriot Insecticide Cattle Ear Tag Safety Data Sheet. Revised Mar. 3, 2021.
Patriot Insecticide Ear Tag for Cattle, Template for Relevant Label Particulars, AP/MA approval No. 53910/0507, Australian Pesticides and Veterinary Medicines Authority.
Powell, "Lidocaine and Lidocaine Hydrochloride", Analytical profiles of drug substances, 1986, 15: 761-779.
Ramchandra, Atul M et al., "Pyrethroid Poisoning." Indian Journal of Critical Care Medicine, Dec. 2019; vol. 23.4 pp. 267-271.
Roche et al., Efficacy of a lidocaine impregnated elastrator band for castration and tail-docking in lambs, Animals 2023, 13, 13 pages.
Ross et al., Assessment of the effective tissue concentrations of injectable lidocaine and a lidocaine-impregnated latex band for castration in calves, Animals 2023, 13, 12 pages.
Ross et al., Assessment of the Effective Tissue Concentrations of Injectable Lidocaine and a Lidocaine-Impregnated Latex Band for Castration in Calves, Animals 2024, 14, 977, 12 pages.
Ross et al., Assessment of the Pharmacokinetics and Pharmacodynamics of Injectable Lidocaine and a Lidocaine-Impregnated Latex Band for Castration and Tail Docking in Lambs, Animals 2024, 14, 255, 13 pages.
Saville et al., "Development and Field Validation of Lidocaine-Loaded Castration Bands fo rBovine Pain Mitigation", 2020, Animals, 10(12): 2363.
Sevgi et al., "Antibacterial effects of lidocaine and adrenaline", Int Wound J, 2019, 16: 1190-1194.
Song, Weizhong et al., "Analyasis of the action of lidocaine on insect sodium channels". Insect Biochemistry and Molecular Biology, Sep. 17, 2010, vol. 41.1, pp. 36-41.
Stewart et al., Do rubber rings coated with lignocaine reduce the pain associated with ring castration of lambs?, Applied Animal Behaviour Science 160 (2014), pp. 56 to 63.
Svena et al., "Local Anesthetics as Antimicrobial Agents: A Review", Surgical Infections, 2008, 9(2): 205-213.
The Use of Insecticide-Impregnated Cattle Ear Tags on the Halters of Horses, Ontario Ministry of Agriculture, Food and Rural Affairs. Accessed Nov. 28, 2022.
Y-Tex Agressor Approved E-Label, RLP. APVMA Approval No. 62199/119798.
Y-Tex Optimizer Approved E-Label, RLP. APVMA Approval No. 46406/119795.
Y-Tex Optimizer Product Information Sheet, Y-Tex Corporation.
Y-Tex Optimizer Safety Data Sheet, MSDS. Printed Oct. 13, 2015.
Y-Tex Python Approved E-Label, RLP. APVMA Approval No. 48148/119796.
Y-Tex Python Maxima Approved E-Label, RLP. APVMA Approval No. 57920/119799.
Y-Tex Python Maxima Product Information Sheet, Y-Tex Corporation.
Y-Tex Warrior Approved E-Label, RLP. APVMA Approval No. 51524/119797.

(56) References Cited

OTHER PUBLICATIONS

Y-Tex Warrior Product Information Sheet, Y-Tex Corporation.
Y-Tex Warrior Safety Data Sheet, MSDS. Printed Oct. 13, 2015.

* cited by examiner

LIGATURE DEVICE AND METHOD OF USE

TECHNICAL FIELD

This invention relates to an apparatus and method for ligation. The ligation device incorporates and provides a topical active agent(s) that alleviates pain during various ligature procedures.

This invention also relates to a method that includes applying a ligation device around a body part for ligation, whereby the material of the device supplies a topical active agent(s) to the body part to reduce the pain of ligation. Preferred examples of ligation devices of the invention include elastomeric loops or bands commonly used for castration and docking by ligation in animals.

BACKGROUND

Ligation with an elastic band, or "elastration", is a bloodless method of male castration and docking commonly used for livestock. Elastration involves placing a tight elastic band, or elastrator, around the body part of an animal to reduce the blood flow to the part so that it withers and falls off. To reduce the discomfort to the animal during this procedure, either the elastration band or the body part or both can be coated with an anesthetic such as lidocaine prior to placement on the animal. The secondary step of applying anesthetic during elastration adds cost, inventory and labor to the procedure that could be avoided if the anesthetic could be incorporated into the elastration band itself. The topical agents that are applied during elastration provide only temporary pain relief that wears or washes off quickly and must be reapplied to provide prolonged pain relief during the entire elastration period.

In other known procedures, lidocaine is injected into the animal body part. This injection typically provides only about three hours of pain relief, in contrast to the present invention which may provide pain relief for 21 days or longer.

Notwithstanding the usefulness of the above-described methods, a need still exists for better methods of reducing the pain and stress to an animal undergoing elastration.

SUMMARY

This invention provides a device for use in ligation procedures, wherein the device comprises at least one active agent or active agent composition for the treatment of pain. A preferred embodiment of the invention is an elastomeric band or loop for elastration that contains one or more active agents to reduce the pain of elastration.

An advantage of the invention is the band dispenses a localized analgesic/anesthetic over time that provides extended duration pain relief for animals undergoing ligation or castration, or for any animal undergoing any procedure that would benefit from the application of a local analgesic/anesthetic through a band.

The present invention discloses a method and apparatus for ligation that avoids or alleviates the problems discussed above. The present invention provides a ligature band (with active agent(s)) for attachment to an animal body or part thereof where the band or a part thereof releases the active agent(s). The release of the active agent reduces the pain and or stress to the animal, and may also reduce the likelihood of swelling and infection.

The purpose of this invention is to produce an elastration band that contains one or more agents that relieve pain, (e.g., anesthetics and analgesics) so that both the band and the active agent(s) are applied simultaneously to the animal. An anesthetic such as lidocaine can be incorporated into the elastration band by several methods. The agent can be coated onto the band, infused into the material of the band, or inserted into the center of a hollow elastration band.

With the following enabling description of the drawings, the apparatus should become evident to a person of ordinary skill in the art.

DETAILED DESCRIPTION

Figure 1:
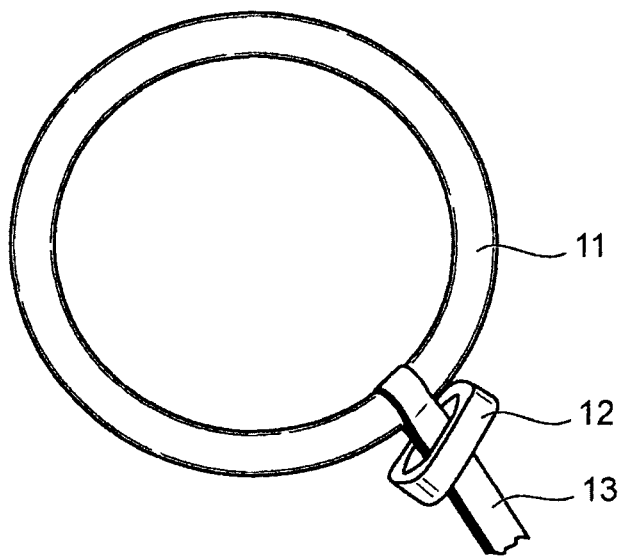
FIG. 1 shows an embodiment of the invention in which the ligation apparatus is a band, and the apparatus includes a cinch pull.

The present invention is a ligation device that elutes or delivers one or more active agents, wherein the device provides topical or local pain relief. In preferred embodiments of the invention, the device comprises an elastomeric tube or band containing one or more active agents. In some embodiments of the invention, the band itself elutes the active agent(s). In preferred embodiments of the invention the ligation device is an elastration band.

Active agents, as used herein, refer to one or more analgesics; one or more anesthetics; one or more antibiotics; one or more skin permeation or penetration enhancers; one or more anti-inflammatory agents; one or more hormones; one or more chemical indicators, e.g., visual or performance indicators; one or more vasoconstrictor agents; and combinations thereof.

Band, as used herein, refers to a band, ring, tube, straw, conduit, or the like. In some embodiments, the band is a length of tube or rubber having two ends; in these embodiments, the band may also include one or more fasteners and/or one or more crimpers or clamps. In other embodiments, the band is a closed loop. In preferred embodiments of the invention, the band is elastomeric. The band of the present invention is described in more detail below.

The present invention is also a method of making a ligature band comprising dissolving one or more active agent(s) or a composition comprising one or more active agents in a solvent or solvent composition, then soaking or contacting the band in the solvent/active agent composition. The band swells in the solvent and absorbs the active agent(s), then the solvent is evaporated, trapping the agents in the band, and thereby providing an active agent-eluting band.

In preferred embodiments, the solvent formulation also contains an additional skin permeation enhancer. In other embodiments, the method uses a solvent formulation that contains one or more additional active agents dissolved in the formulation.

Another embodiment of the present invention involves a band or tube of a predetermined length or diameter comprised of an elastomeric material wherein the material comprises one or more active agents suitable for providing a beneficial topical treatment for the animal.

A preferred embodiment of the invention comprises an elastomeric band, e.g., a band made from rubber, that is coated or infused with lidocaine. In a preferred embodiment, the band contains an analgesic/anesthetic and a skin permeation enhancer. In these embodiments of the invention, the band releases its active agent over time (i.e., controlled release of active agent(s)). As used herein, controlled release refers to the release of active agent over time. This period may be 21 days or longer depending on the active agent composition. Controlled release is at least 1 day, preferably at least 5 days, and most preferably up to about 15 days. In typical use, the band stays on until the body part falls off.

In accordance with the present invention, the apparatus or band elutes or delivers a sufficient amount of active agent to provide quick action onset, as well as prolonged duration of the active agent activity. One skilled in the art will recognize that an effective amount, quick action, onset, and duration are all characteristics that may vary or interact in achieving a band having analgesic properties.

The present invention is treating an animal to prevent or mediate pain by applying an agent-eluting band to an animal or body part in need thereof. Some embodiments of the invention include treating an animal to prevent or mediate pain and infection by applying a device of the present invention.

A band of the present invention may be placed on the animal by hand, or may be placed on the animal using a device or applicator. In the embodiments in which the band is placed using an applicator, the band and applicator may be configured and adapted to work together, as is well known in the art.

Alternatively, the present invention may also involve a method of treating an animal in pain comprising administering or applying a ligation apparatus or an elastomeric material of the present invention.

The present invention also may involve an elastrator or ligation band comprising an elastomeric material comprising at least one active agent for the topical treatment of pain.

The elastomeric band may comprise any material that is suitable or medically appropriate for use as a ligation band as described herein. Typical elastomeric materials include but are not limited to rubber (natural, synthetic, or silicone) or thermoplastic elastomers, including polybutadiene, polyisoprene, polychloroprene, nitrile, SBS, SEBS, EPDM, and polyurethane. The band may be solid, hollow, porous, or tubular (e.g., defining a lumen). In embodiments of the invention where the band is tubular, the anesthetic may be infused into the material, contained within the lumen of the tube or both infused into the material and contained within the lumen.

In other embodiments of the invention, the band includes a second band or sleeve that elutes or delivers the active agent.

In embodiments of the invention that include a sleeve, the sleeve is solid, hollow, porous, or tubular (e.g., defining a lumen). In some embodiments, the sleeve may be a layer or coating.

Some embodiments of the invention also include one or more additional active agents that are capable of being transferred to the body part after contact with the band. The additional active agent(s) include, but are not limited to, one or more of the following: a second analgesic agent, such as Meloxicam, an anesthetic agent, an anti-inflammatory agent, antimicrobial agent, an antibiotic, a hormone, or combinations thereof.

A band of the present invention includes at least one active agent that is capable of being transferred to the body part after contact with the band or sleeve. In preferred embodiments, the active agent is a local anesthetic or analgesic, or is a composition that includes a local anesthetic and/or analgesic. A suitable or exemplary anesthetic or analgesic includes, but is not limited to one or more of the following: lidocaine or meloxicam.

A band of the present invention also includes a permeation enhancer. As used herein, a permeation enhancer refers to a substance or chemical that increases or modulates absorption of an active agent by the skin of the animal. To enhance local anesthesia, chemicals that increase the percutaneous penetration of the anesthetic are also incorporated into the elastration band. Such permeation enhancers are known to the art of transdermal drug delivery. For the example of an elastration band containing lidocaine, useful permeation enhancers include but are not limited to: fatty acids (e.g. palm oil); fatty acid esters (e.g. isopropyl myristate); poloxamers (e.g. poloxaline), triglycerides (e.g., amine oxides, such as cocamine oxide), n-methyl pyrrolidone, povidone, terpineol, DMSO, and dimethylacetamide. Because of the hydrophobic nature of skin, the free base of lidocaine is used rather than a more polar lidocaine salt to enhance skin penetration. The inventors believe that permeation enhancers are not typically used in elastrator bands.

One skilled in the art will recognize that the choice of permeation enhancer is tied to the particular analgesic or anesthetic being used and may also be selected based on its ability to diffuse from the elastomeric band. Suitable permeation enhancers for lidocaine are described in Mohammadi-Samani, et al.; Pak. J. Pharm. Sci., Vol. 23, pp 83-88 (2010), incorporated herein by reference.

Some embodiments of the invention include one or more anti-inflammatory agents. Anti-inflammatory agents include but are not limited to non-steroidal anti-inflammatory drugs (NSAIDs) such as meloxicam, flunixin, ketoprofen, diclofenac, and ibuprofen. Steroidal anti-inflammatory agents include but are not limited to dexamethasone, flumethasone, prednisolone, prednisone, and immune selective anti-inflammatory derivatives (IMSAIDs). The inventors believe that anti-inflammatory agents are not typically used in elastrator bands.

Some embodiments of the invention include one or more hormones. Hormones include but are not limited to cortisone, hydrocortisone, trenbolone, testosterone, and estradiol. The inventors believe that hormones are not typically used in elastrator bands.

Some embodiments of the invention include vasoconstrictive agents such as epinephrine, pseudoephedrine, phenylephrine, thromboxane and angiotensin. Vasoconstrictor agents for use in the invention are known by those with skill in the art.

Some embodiments of the invention also include one or more chemical indicators such as dyes, pigments, pH indicators or stains to further differentiate that the bands contain active agent(s). These chemical indicators could also release with the active agents to provide visual evidence of active agent release to the area of application. In some cases, the chemical indicator may also be an active agent. Examples include, but are not limited to the use of antimicrobial dyes such as gentian violet, which stains the area a blue-purple color and also acts as a topical antimicrobial agent that helps prevent infection at the site of elastration. In other examples the chemical indicator includes the use of pH indicators to identify alkaline pH, which is correlated with infection. Examples of other chemical indicators that could be incorporated into devices of this invention include, but are not limited to, Nile Red, Oil Red, Sudan Red, Congo Red, cresol red, Coomassie Red, Coomassie Blue, methylene blue, Oil Blue, gentian violet, Azure blue, Malachite green, Eosin dyes, Rhodamine dyes, haematolxylin, phenolphthalein, resazurin, phenol red, methyl red, bromothymol blue, thymol blue, alizarin yellow, povidone iodine, and natural dyes such as indigo, turmeric, Catechu and Annatto extract.

The most preferred embodiment of the invention is an elastration band infused with or coated with an anesthetic and analgesic, and a permeation enhancer. The most preferred example is a band infused with lidocaine and isopropyl myristate (1 PM).

The composition comprising at least one active agent may form a coating on the band or may be infused into the band material. A coating may include a powder, liquid, wax, hydrogel or other polymer.

Some embodiments of the invention may also include soaking the band in solvents, such as DMSO (dimethyl sulfoxide) or THF (tetrahydrofuran), to swell the band and cause absorption of the active agents and skin permeation enhancer into the band.

Another method of incorporating anesthetic into elastration bands applies to the use of hollow elastration tubing to construct some larger elastration bands. Anesthetic formulations containing permeation enhancers and other agents including solvents can be incorporated into hollow elastration bands by injection of the solution into the hollow center of the band. A solvent that swells the polymer of the band can be incorporated into the formulation to provide migration of the anesthetic and permeation enhancer through the walls of the band to the surface of the band to provide both fast-acting anesthetic and a reservoir of anesthetic that releases over time. Alternatively, aqueous emulsions of active agents can be used in the center of the tube to prolong the diffusion of active agent. This method is best used in conjunction with coating and infusion methods to provide additional agent(s) for more prolonged release.

Another method of incorporating anesthetic into elastration bands applies to the use of a drug loaded sleeve that is positioned on the band in the area of greatest scrotal tissue contact on the tubular elastrator. The sleeve may be free floating, a partial polymer coating or an adhesive sleeve, each containing anesthetic and permeation enhancers.

Another method of incorporating anesthetic into elastration bands is by compounding the active ingredient into a polymeric material that can be subsequently molded into the devices of the invention using common practices known to the art. As examples, compounding can be achieved with heat and shear, as for compounding into thermoplastic materials, or by mixing with reactive prepolymer components at room temperature, as with silicone rubber, before being molded and cured into the devices of this invention. Typical molding methods include, but are not limited to, injection molding, compression molding, extrusion, reaction injection molding, casting, rotational molding, matrix molding, blow molding, laminating, transfer molding and other methods of thermoforming.

An invention as described herein may include one or more methods of making the apparatus or band. An embodiment of the invention may include a method of making a hollow ligation apparatus comprising introducing into the lumen of the apparatus a solution or emulsion of active agents comprising one or more analgesics; one or more anesthetics; one or more antimicrobial agents; one or more antibiotics; one or more skin permeation or penetration enhancers; one or more anti-inflammatories; one or more hormones; one or more chemical indicators; one or more vasoconstrictor agents; and combinations thereof.

Another embodiment of the invention may include soaking or coating the apparatus in a solution of active agents comprising one or more analgesics; one or more anesthetics; one or more antimicrobial agents; one or more antibiotics; one or more skin permeation or penetration enhancers; one or more anti-inflammatories; one or more hormones; one or more chemical indicators; one or more vasoconstrictor agents; and combinations thereof.

Another embodiment of the invention may include a method of making a ligation apparatus comprising at least one active agent for the topical control of pain, said method comprising the compounding of active agent(s) into thermoplastic elastomers followed by thermoforming.

Another embodiment of the invention may include a method of making a ligation apparatus comprising at least one active agent for the topical control of pain, said method comprising the compounding of active agent(s) into one or more of the unreacted part(s) of castable thermoset resins prior to mixing, casting and curing the resins. In preferred embodiments of the invention, the thermoset resin comprises silicone.

As noted above, a ligation apparatus may be formed or made from various materials. In some embodiments of the invention, the ligation apparatus may be a band; a tube; an elastomeric band or tube; a hollow band or tube; a polymer; a zip-tie; a rope; a rope made from natural material; and a rope made from synthetic material.

In one embodiment, different sized bands are provided in order to perform ligation on different body parts, sizes, types, ages, etc. of animals. A band may also be sized or configured for use with a particular applicator and device. Various devices known in the art employ an endless loop band. Although endless loop bands may accommodate various different size animals and parts, they may present a risk of applying excessive or inadequate tension. An exemplary band is shown in FIG. 1. The illustrated embodiment shows band or tube 11 and also, shows a conventional cinch pull 12 with tab 13.

Figure 2:
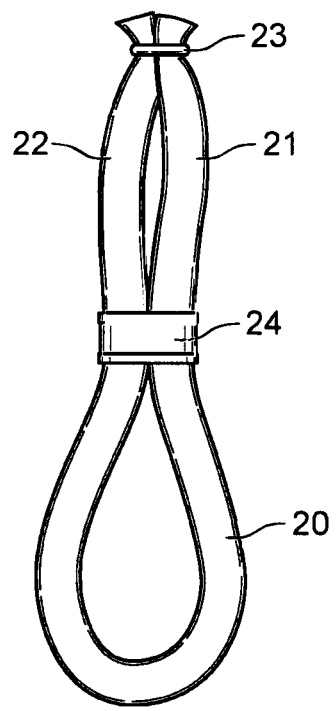
FIG. 2 shows an embodiment of the invention wherein the ligation apparatus is a band or tube having two ends, in which the ends may be fastened together; and wherein the loop may be tightened or closed with a constrictor.

A band of the present invention may be adjustable or adjusted to fit the size and/or shape of the subject animal. An exemplary ligation apparatus is shown in FIG. 2. In FIG. 2, the ligation apparatus 20 is a band or tube having first and second ends, 21 and 22 respectively. The band or tube may be formed into a loop using a fastener or crimp 23. In some embodiments of the invention, the apparatus size may be adjusted using a constrictor 24 or the like.

Figure 3A:
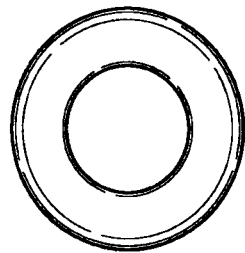
FIG. 3 shows a band configured for larger animals (FIG. 3A), a band configured for intermediate animals (FIG. 3B), and a band configured for small animals (FIG. 3C), any of which can be infused with one or more active agents as described herein.
Figure 3B:
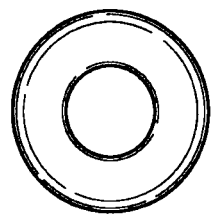
Figure 3C:
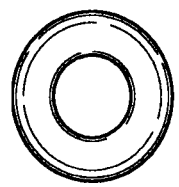

The present invention further contemplates the use of different sized bands. For example, a band is provided that is suitable for ligation of small animals, such as infant calves or sheep (FIG. 3C). A band of similar design is further provided for a medium sized animal, such as a more developed calf. This medium sized band is larger in initial circumference and/or has a higher elastic force (FIG. 3B). Bands may also be provided for larger animals, such as grown bulls (FIG. 3A). These bands may be further color coded and/or labeled so as to readily provide information to a user and reduce the risk of using an improperly sized band, which could result in a failed ligation.

The invention also involves a method for decreasing or modulating pain in animals undergoing a ligation or castration procedure.

Another aspect of the present invention involves a method for ligating a body part of an animal, preferably a tail or scrotum. In preferred embodiments of the invention, the band may be expanded over the body part and released. In some of these embodiments, no tool is required to attach the band to the body part. In other of these embodiments, the band is expanded with a tool before applying over a body part.

Another method involves manually passing a preformed endless loop of ligature material around the body part of the animal. The endless loop is then pulled using various means integral to a ligature tool (e.g., winding mechanisms, pulling mechanisms, etc.) to tighten the loop around the animal's body part. Once the endless loop is sufficiently tightened, it is secured to maintain adequate pressure around the animal's scrotum. Preferably, the step of securing comprises deforming a grommet or other crimping device around the endless loop, while the pulling of the endless loop is accomplished by winding the endless loop around a winding spool integrally attached to the ligature tool. To improve the efficiency and cost of the method, a winding tether and attached hook may be utilized to reduce the overall length of ligature material necessary. After the grommet is deformed around the endless loop to secure the portion of the loop surrounding the body part, the excess ligature material above the grommet may be removed by cutting the part of the loop that is not around the body part with a sharp knife, razor blade or other suitable instrument. Alternatively, the band material can be unwound or otherwise released from the tool, thus eliminating the need to cut the band so as to release it from the tool.

In a preferred embodiment of the invention, the band is an elastomeric material infused with or coated with an anesthetic agent, and the hollow center of the band (if any) is optionally filled with a formulation that includes an anesthetic agent. Suitable anesthetics include but are not limited to lidocaine.

Some embodiments of the invention also include two ends of the predetermined length of the elastomeric material disposed substantially parallel to each other, and an anchor member or tang portion that is secured to the two ends of the elastomeric material of predetermined length, which is used by the ligature tool to tighten the loop around the animal's body part. In such embodiments, a crimping band is also provided, the crimping band being translatable along at least a portion of the length of a band in an un-crimped state. After the loop is tightened around the body part, the band is crimped to hold the two ends of the loop in place and the excess material may be trimmed from the attached loop.

One skilled in the art will recognize that a band of the present invention may be incorporated into a system according to the invention. A system of the present invention may include, but is not limited to one or more of the following: packaging, the band, a vial or the like of anesthetic; and a vial or the like of permeation enhancer.

One skilled in the art will recognize that the invention as described herein may be reconfigured into different combinations, elements, and processes that are included within the scope of the invention.

This invention is in the general field of methods and apparatus for non-surgical removal of animal tails, horns, testicles, and the like. It is further directed to the foregoing mentioned field wherein a resilient ring of rubber, or the like, is formed, having is very small opening but being expandable to slip over the portion of the animal to be non-surgically removed and then released onto such member so as to completely cut-off the flow of blood from the main portion of the animal to the member, at the same time pulling the skin adjacent the animal into a configuration such that the skin covers the area from which the member was removed. The invention is even further directed to the non-surgical removal of tails from swine by expanding the ring in a unique triangular configuration by utilization of a unique ring expanding tool and applying the ring around the tail of the swine and removing the ring from the expanding tool.

EXAMPLES

Method 1: Soaking Solution

An elastic band or tube made for elastration of animals is soaked in a volatile organic solvent solution that contains at least one anesthetic or analgesic and one skin penetration enhancer. Both the anesthetic and the skin penetration enhancer (the "agents") are completely dissolved in the solvent. The solvent swells the material of the elastic band and carries the two agents into the elastic material of the band by diffusion. The bands are soaked in the solution until equilibrium swelling of the band and diffusion of the agents into the material of the band has been achieved. The bands are then removed from the solution and air-dried. Drying may also be accomplished in an oven. This causes the volatile solvent to evaporate, trapping the agents within the material of the band. The evaporative drying process may also bring both the anesthetic and the skin penetration enhancer to the surface of the device, where they remain as a coating on the band surface. This coating provides readily available anesthetic with skin penetration enhancer for when the band is first applied to an animal, while higher concentrations of the agents residing in the material of the band and are released more slowly over time as the band is worn by the animal, providing long term anesthetic activity.

Example 1

A solid elastration band made of latex rubber is soaked for 24 hours in a solution containing 25% by weight lidocaine free base, 25% by weight isopropyl myristate (1 PM), a skin penetration enhancer, and 50% by weight of the volatile organic solvent tetrahydrofuran (THF). The band is then removed from the solution, air-dried for 3-4 hours and dried in an oven at 170° F. for 30-60 minutes before it is packaged for use.

Example 2

A latex rubber elastration band is soaked as described in Example 1 except that the solution contains 30% by weight lidocaine free base, 20% isopropyl myristate and 50% THF.

Example 3

A latex rubber elastic band is soaked as described in Example 1 or 2 except that the solution also contains one or more skin permeation enhancers in a combined amount from 1-50% of the solution. Skin permeation enhancers used by the invention may include (but are not limited to) terpineol, limonene, esters derived from palm kernel oil, dimethyl sulfoxide (DMSO) and n-methyl pyrrolidone.

Example 4

A latex rubber elastic band is soaked as described in Examples 1-3 except that the solution also contains from 1 to 10% of a water-soluble excipient or surfactant to facilitate migration of the lidocaine to the surface of the band. Examples of these additives include, but are not limited to, glycerol, propylene glycol, polyethylene glycol, polypropylene glycol, nonoxynol 9 and other surfactants.

Example 5

A latex rubber elastic band is soaked as described in Examples 1-4 except that the solution also contains a second anesthetic or analgesic agent in an amount from 1-20% of the solution. Secondary anesthetic or analgesic agents useful for the invention include, but are not limited to, lidocaine HCL or other salt, bupivacaine, levobupivacaine and meloxicam. Other agents that enhance or prolong the action of the primary anesthetic may also be incorporated into the solution. One such agent that prolongs the activity of bupivacaine is epinephrine.

Example 6

A latex rubber elastration band is soaked as described in Example 1 except that the solution contains 20% by weight of the slow releasing lidocaine free base, 10% by weight of the water soluble and fast releasing lidocaine hydrochloride, 20% by weight isopropyl myristate (1 PM), a skin penetration enhancer, and 50% by weight of the volatile organic solvent tetrahydrofuran (THF).

Example 7

A latex rubber elastic band is soaked as described in any of the examples above except that the solution also contains a second active agent in an amount from 1-20% of the solution. Examples of these active agents are an antimicrobial agent, an antibiotic, an anti-inflammatory agent, a vasoconstrictor or a hormone.

Example 8

A latex rubber elastic band is soaked as described in any of the examples above except that the solution also contains a dye, pigment, stain or pH indicator to act as a chemical indicator of agent release in an amount from 0.1-5% of the solution. In a preferred example, the chemical indicator is gentian violet, and it also acts as an antimicrobial agent.

Example 9

Silicone or other synthetic rubber elastic bands are soaked as described in any of Examples 1 through 8.

Example 10

A thermoplastic polymer is compounded with one or more active agents as described in the examples, and the compounded material is used to injection mold the bands of the invention.

Example 11

A thermoplastic polymer is compounded with one or more active agents as described in the examples, and the compounded material is used to extrude tubing that is cut into sections that become the elastration bands of the invention.

Example 12

One or more of the active agents described in the examples are compounded into silicone resin prepolymers, and then cast into molds or extruded into tubing and cured at elevated temperatures to fabricate the elastration bands of the invention.

Method 2: Injected Solution

Elastration bands are often made from hollow rubber tubing. For these bands a different method may be used to infuse anesthetics and skin penetration enhancers.

Any of the solutions, anesthetics, skin penetration enhancers and other agents described in Method 1 may also be used in Method 2. Rather than soaking the elastration band in a solution, the band may be treated by filling the tubing with the solution and allowing time for it to swell the tubing and infuse its rubber material with the agents. This can be accomplished in bulk with a long piece of tubing before it is cut into sections that are formed into circular bands, or the solution can be injected into the hollow center of the tubing after the elastration band has been formed by fixing the two ends of a tubing section together. This method may also be combined with Method 1 by filling tubing previously coated as described in any of Examples 1 through 12. The tubing may also be filled with aqueous emulsions of active agent(s) and skin penetration enhancers. Such emulsions may be used in combination with the devices from Method 1 to provide an additional reservoir of active agent for prolonged release.

Example 13

A length of hollow tubing is filled with any of the solutions from examples 1 through 8, and the tubing is allowed to dry in air or in an oven until all of the organic solvent has evaporated. Evaporation may be facilitated with heat and vacuum, as, for example, in a vacuum oven. Once the tubing has dried, a section of it is cut and the ends of this section are fastened together to make an elastic loop that may be used as an elastration band.

Example 14

The ends of a section of hollow tubing are fastened together to make a loop that may be used as an elastration band. Any of the solutions described in examples 1 through 8 are then injected by a syringe into the hollow center of the band. The band is then dried to remove the volatile organic solvent. Drying may be accomplished as described in Example 13. The band may be rotated during drying to provide a more even distribution of the anesthetic agent in the band during drying.

Example 15

An aqueous emulsion of active agent(s), skin penetration enhancers and, optionally, solvent, is used in place of any of the solutions from examples 1 through 8 to fill the hollow center of the tubing in Examples 8 and 9. The bands may or may not be dried, depending on whether a solvent that needs to be removed is used in the emulsion formula.

Method 3: Molding Formulations

Elastration bands containing an active agent composition may also be fabricated by compounding active agents into thermoplastic materials using heat and shear, followed by fabrication of the elastration bands by common methods of thermoforming.

Example 16

Active agents as described in any of Examples 1-8 are compounded into any one of a number of elastomeric polymers or thermoplastic elastomers using heat and shear by common methods such as, for example, twin-screw compounding. The resulting compounded material is then used to injection mold elastration bands, or the compounded material is extruded into tubing that is then cut into small sections and used as elastration bands.

Example 17

Active agents as described in any of Examples 1-8 are compounded into liquid silicone rubber (LSR) and used in reaction injection molding or extrusion to form elastration bands or tubing, respectively. The extruded tubing is cut into sections that are used as elastration bands.

Example 18

Active agents as described in any of examples 1-8 are compounded into a thermoset rubber or elastomer formulation, and molded or extruded to make elastration bands by reaction injection molding (RIM).

Example 19

Any of the compounded formulations of Examples 16-18 may also be coextruded over other materials to make ligation devices of the invention. In one preferred example, the compounded material is extruded over wire to produce twist ties that contain active agents and can be used for ligation. In another example, the compounded material is extruded over a polypropylene core to produce zip-ties that can be used for ligation.

Method 4: Casting Formulations

Elastration bands containing an active agent composition may also be fabricated from castable rubber or other castable elastomers. For this method the agents are mixed with the liquid prepolymer formulation before it is mixed with an activator that produces polymerization and crosslinking to cure the formulation into a solid. After adding the activator, the formulation is then cast into a mold to form a ring or band that can be used as an elastration device. Once the formulation has been cast into a mold it is cured, typically by heating in an oven, to produce the finished elastic band containing the anesthetic and skin permeation enhancer.

Example 20

A castable, two-part RTV silicone rubber is used, and the anesthetic agents, skin permeation enhancers and other ingredients are compounded into one or both parts of the formulation by mixing, before the two parts are mixed together to begin the curing process. After mixing the two parts, the formulation is then cast into a mold where the RTV silicone cures into an elastic silicone rubber containing the active agents.

Curing of the rubber may be accelerated by heating in an oven. Any of the agents described in examples 1 to 8 may be used.

Example 21

Formulation Development: Formulations containing 25% lidocaine (w/w) were prepared with four different skin penetration enhancers (SPE), (terpineol (TP), DMSO, 1 PM, and N-methyl pyrrolidone (NMP) being used at 33% of total solvent in THF (i.e., 33:67 SPE:THF). Four-inch sections of a latex catheter were affixed in a "U" to a metal wire and coated by soaking the U-section in each formulation. They were then removed from solution and allowed to air dry for 48 hrs to evaporate all THF. Based on the observations of coating quality and the length of coating on the tube, it was determined that the formulation containing 1 PM produced the best coating, with terpineol a close second. DMSO produce about half the coating length of 1 PM and TP, while NMP was the worst coating solvent and produced very little surface coating.

Example 22

Soak Coating: Initially, bands were swollen in coating formulations overnight to ensure equilibrium swelling and maximum uptake of lidocaine. When swelling of the bands was studied as a function of time in the coating formulation, it was found that 3 hours of swelling at room temperature produced near-equilibrium swelling that was sufficient to incorporate lidocaine into the band.

Example 23

Secondary Coating and Drying with Heat: Because THF evaporates rapidly, coated bands could be dried in air for a few hours, then the remainder of THF could be removed more quickly by drying in an oven with low heat. The final drying method combined air drying with oven drying to remove all of the THF while retaining most of the 1 PM in the band. After experimenting with different lengths of air-drying time from 1 to 3 hours combined with 15 to 60 minutes oven drying at 170° F., it was found that 2 hours of drying in air followed by 30 minutes of oven drying eliminated the THF from the coating while maintaining a high percentage of the 1 PM. This is the drying method presently being used for the small green elastration bands. Bands of higher mass will require longer drying times.

Example 24

Extractables from rubber: It is known that strong solvents like THF that swell rubber will extract some low molecular weight unreacted components of the rubber. These extractables concentrate in a coating formulation as the number of elastration bands that is soaked in the formulation increases. When the extractable concentration becomes too high in the formulation, it must be discarded and replaced with a fresh coating solution. This adds cost to the coating for each device. The addition of a small amount of a non-solvent for rubber such as water or alcohol can reduce the amount of extractables in a THF coating formulation over time. In an effort to reduce rubber extractables, water was added to the lidocaine:IPM:THF formulation in amounts from 1 to 5% (w/w) based on the total solvent in the composition. Lower percentages of water (1-3%) were found to be well tolerated by the formulation, but at higher percentages (4-5% water) lidocaine tended to precipitate from solution. To reduce lidocaine precipitation, a combination of 5% ethanol, which is a nonsolvent for rubber but a good solvent for lidocaine, and 1% water was used in place of an equal amount of THF in the current formulation, and this produced a formulation that did not precipitate lidocaine. The effect of these non-solvents on the % extractable from rubber has yet to be evaluated, but it is anticipated that the inclusion of ethanol and water will reduce extractables in the manufacture of coated elastration bands, allowing longer use of coating solutions.

Example 25

Preferred method for making lidocaine-loaded small green elastration bands: Fifty green elastration bands were soaked for three hours in coating solution composed of 25.9% lidocaine, 22.8% 1 PM, 48.2% THF, 2.6% ethanol, and 0.50% H2O, and then hung to air dry in a hood for 3 hours. The rings were then dried in an oven at 170° F. for 30 minutes. After cooling, the rings were sealed in foil pouches.

Example 26 lidocaine loading: Sample bands made to study the effect of nonsolvents on the coating formulation were evaluated for total concentration of lidocaine contained within the bands. Concentration of lidocaine contained within the bands was determined by high performance liquid chromatography (HPLC, United States Pharmacopoeia USP 29-NF24 Page 1253). Test bands were placed in an appropriate vial with 15 ml of THF and a magnetic stir bar. These bands were extracted for 4 hours, then 2.5 ml of the extraction sample was added to 50 ml of mobile phase (75% buffer and 25% acetonitrile). lidocaine concentration was determined by comparing unknown sample data to a five-point standard calibration curve. lidocaine loading results based upon the results of HPLC analysis are presented in Table 1, and showed that lidocaine loading decreases with the addition of nonsolvent to the formulation.

TABLE 1

HPLC results demonstrating lidocaine loading in the ring as a function of solvents utilized.

| | Solvents | | | | |
|---|---|---|---|---|---|
| % Lidocaine | % THF | % IPM | % Ethanol | % H2O | Lidocaine (mg/ring) |
| 25 | 66.6 | 33.4 | | | 79.1 |
| 25 | 66.6 | 33.4 | 6.7 | | 69.2 |
| 25 | 66.6 | 33.4 | 6.6 | 1.4 | 55.8 |

As determined by HPLC, good loading of lidocaine into ligation bands is possible utilizing various methods as described herein.

Example 27

Use of ligation band to provide lidocaine that alleviates pain during castration Small (4.3 cm) green elastrator bands with a lidocaine made in Example 25 were tested in calves less than 200 pounds. This study investigated the efficacy of the prototype lidocaine elastration bands by assaying the lidocaine levels remaining in used devices and in skin biopsies at the site versus time of use on the animal. Indicators of pain in the animal were used to assess the duration a therapeutic lidocaine level was maintained. Welfare observation techniques were also tested that included physiology (temperature of affected site, weight) and behavior (continuous electronic (motion and pedometers to measure tail flicks)). 24 animals were assigned to the test group (A: animals treated with a lidocaine containing elastration band) and 24 animals were assigned to the negative control group (B: lidocaine 20 mg/ml injection at the site, with an untreated elastration band). Rings were removed and tissue samples taken at various time points post ligation application (0.5, 1, 2, 4, 6, 24, 48, and 168 hours).

Average Daily Gain

Average Daily Gain (ADG) was calculated for Day 7 calves. The difference from the pre-castration weight collected on day 0 was divided by 7, the number of days since day O (Table 2). The average on day O for the entire group (treatment and control) was 53.4 kg and on day 7 the average was 59.1 kg. Band type A group (Lidocaine band) had an ADG of 0.886±0.647 kg/day and Band type B (plain band) had an ADG 0.729±0.272 kg/day.

TABLE 2

Average daily gain post castration by treatment group (Control B vs Test A).

| Animal | Weight Day 0 (Kg) | Weight Day 7 (Kg) | ADG (kg/day) | Test Group |
|---|---|---|---|---|
| 41 | 54.8 | 60.9 | 0.871 | B |
| 43 | 53.5 | 59.8 | 0.900 | B |
| 45 | 49.7 | 52.6 | 0.414 | B |
| 40 | 51.8 | 62.8 | 1.571 | A |
| 42 | 49.3 | 51.3 | 0.286 | A |
| 44 | 61.5 | 67.1 | 0.800 | A |

| Summary | | |
|---|---|---|
| | ADG (kg/day) | ±SD |
| Control (B) | 0.729 | 0.27 |
| Test (A) | 0.886 | 0.65 |

The slight increase in ADG in the test group indicates that the lidocaine eluting band did not have any negative impacts on animal behavior and may indicate pain mitigation associated with the lidocaine release by improved ADG (Marti et al, 2017).

Increased Tail-flicking

Increased Tail-flicking is an indicator of discomfort (Moya et al, 2014), so pedometers attached to animal tails were used on all animals to determine tail movements. Pedometer values were collected and recorded at three time points, 0.5 hours, 6 and 48 hours after treatment (See Table 3). The Tail Flick data was organized into the treatment groups (A: Lidocaine Elastration Band and B: Injection lidocaine with plain band) at the different time points. There were three animals assigned to each treatment group and time point. The average difference between the treatment groups was 15,885 for the 0.5 hr time point, 15,718 for the 6-hour time point and 56,940 for the 48 hour time point. This data suggests pain mitigation associated with the lidocaine release by reduced tail flicks, which was especially significant at the 48 hrs time point, where the injected lidocaine of the Control would no longer be providing anesthesia (Moya et al, 2014).

TABLE 3

Pedometer values overtime (post elastration placement) from tail attachment as an indicator of discomfort through tail movement. (A: Lidocaine Elastration Band prototype, B: injection lidocaine with plain band)

| Sample Group* | Group | Number of tail swings | Difference (Cotnrol-Test) |
|---|---|---|---|
| 0.5 hours | Control (B) | 26,437 | 15,885 |
| | Test(A) | 10,552 | |
| 6 hours | Control (B) | 18,513 | 15,718 |
| | Test(A) | 2,795 | |
| 48 hours | Control (B) | 89,559 | 56,940 |
| | Test(A) | 32,619 | |

*Time in hours the pedometer was stopped, and data recorded.

Tissue Temperature at Site

Temperature measurements over time were also made in the animal study of Example 27 to provide evidence of reduced inflammation and blood flow. Inflammation and blood flow are indicators of pain and healing at a wound site (Melendez et al, 2017). Images of the scrotal area, specifically the neck, were captured below and above the placement of the elastration bands applied in Example 27 using a thermal imaging camera (FLIR E75-42). The temperatures registered and recorded by the thermal camera of the target scrotal areas, above and below the elastration band, were recorded over the course of the study. The temperature in Celsius is plotted for the test and control animals over time. For the first 48 hours there was no difference in the two groups. The average temperature above the band for the Control subjects was 36.39° C. and for the Test group was 36.36° C. Below the elastration band the average was 31.27° C. for the Control and 31.85° C. for the Test. At the longer time point of 144 hours (day 7), the average temperatures were higher for the control group, with the below the band temperature at 32.47° C. for the Control, compared to 30.03° C. for the Test Group. The decreased temperature below the ligature band over time indicates proper ligature function and supports the claim of the invention functioning in this capacity. The reduced temperature of the lidocaine containing ligature band compared to the control band indicates reduced inflammation, which should correlate with reduced pain in the animal.

Figure 4:
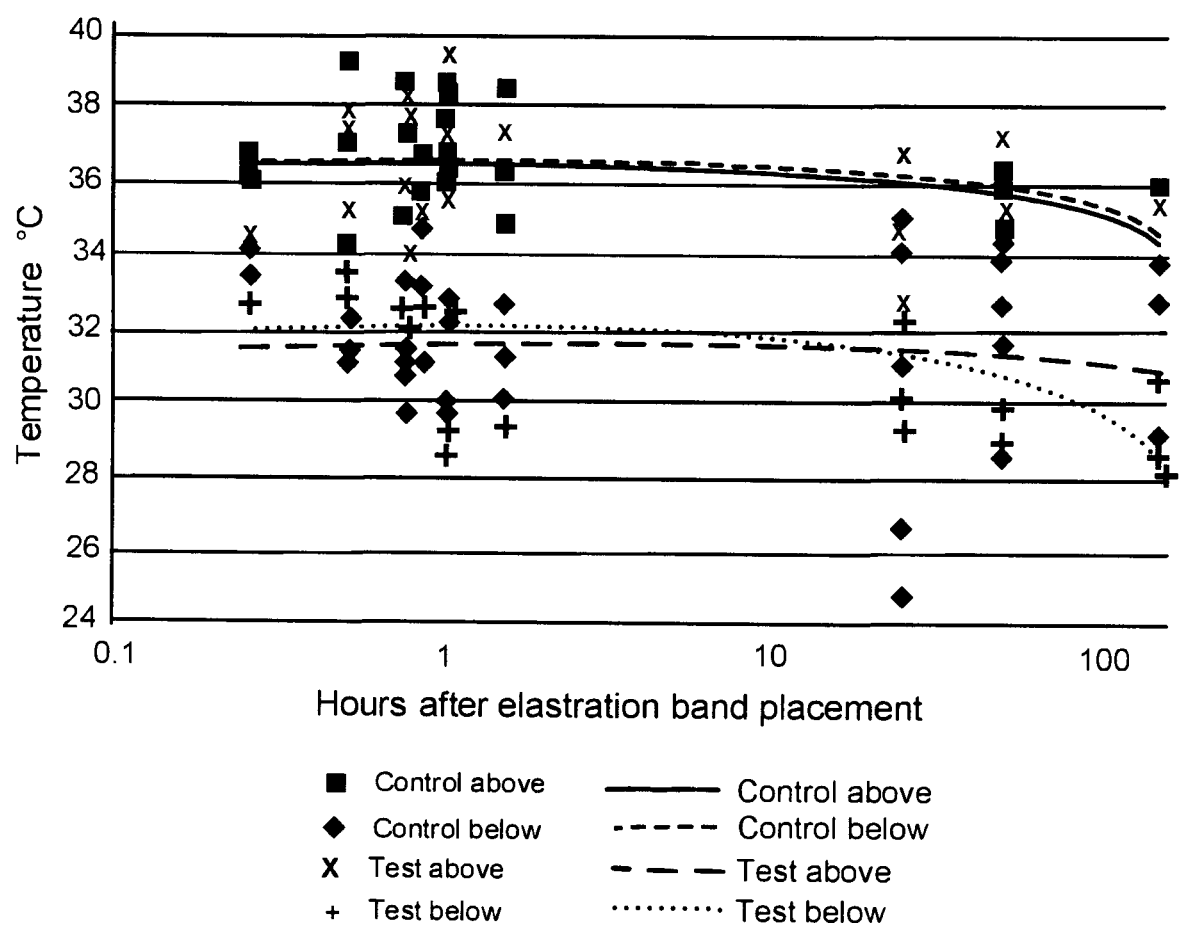
FIG. 4 shows temperature above and below the elastration band as measured at various intervals (hours) after application of the ligation apparatus.

FIG. 4 shows temperature above and below the elastration band as measured at various intervals (hours) after application to the scrotum. Control (injected lidocaine with unmedicated band) and Test (lidocaine elastration band) subjects' data are plotted as squares and diamonds for the control treatment and 'x' and '+' for the test treatment. Trend lines for each data set are also depicted. This data demonstrates two important elements: A) the reduction in blood flow (as measured by temperature decrease) is greater in the test group over time compared to the control indicating improved performance, and B) the reduced temperature over time indicates that the bands function properly to reduce blood flow and cause castration by constriction.

Analysis of Lidocaine in Tissue: Tissue lidocaine levels obtained from tissue biopsy samples taken directly underneath the elastration bands over time (post elastration placement) as determined by HPLC analysis demonstrates that the test bands (group A) deliver effective concentrations of lidocaine (Yoshida et al, 2016) to the tissue over the 48-hour sampling period versus the control, which only delivered effective lidocaine levels at the 6-hour time point. The levels of lidocaine associated with the tissue in the test group is significantly higher than in the control group at 24 and 48 hours, and is detected at levels capable of producing a therapeutic effect (Table 4).

TABLE 4

Tissue lidocaine levels obtained from tissue biopsy samples taken directly underneath the elastration bands over time (post-elastration placement, as determined by high performance liquid chromatography (HPLC) analysis), as an indicator of lidocaine delivery to tissue. (A: lidocaine Elastration Band prototype, B: Control, injection lidocaine with plain band).

| | MEAN (mg/g) | ±SD |
|---|---|---|
| 6 hr sampling | | |
| CONTROL (B) | 0.5610 | 0.19 |
| TEST (A) | 0.2500 | 0.32 |
| 24 hour sampling | | |
| CONTROL (B) | ND | NA |
| TEST(A) | 0.0919 | 0.04 |
| 48 hour sampling | | |
| CONTROL (B) | 0.0069 | NA* |
| TEST (A) | 1.0286 | 1.16 |

*only 1 sample of three had detection of lidocaine above the 0.0005 mg detection limit
(SD = standard deviation, sampling n = 3 per treatment group
ND = not detected (below the 0.0005 mg/g HPLC detection limit),
NA = Not Applicable)

Tissue Collection And Processing Methodology

Rings were removed and tissue samples (4 mm biopsy punches) taken at various time points post ligation application (6, 24, and 48 hours) in the animal study of Example 27. Biopsy samples were dissolved in 2 ml 1 M NaOH at 37° C. for 3 hours. The sample was then neutralized by the addition of HCl. A liquid-liquid extraction procedure is conducted as follows: 0.01 ml of a 120 mg/ml solution in 95% ethanol of an internal standard (tetracaine) is added to the homogenized tissue sample, and the sample is vortexed for 15 seconds. 5 ml of ethyl ether is then added, and the sample is vortexed again for 15 seconds. The ether layer is allowed to separate for 2 minutes, then it is removed and evaporated to dryness. The residue is then dissolved in 1 ml of HPLC grade methyl alcohol, and HPLC analysis is conducted. Effective tissue concentrations in the tissue are typically between 0.150 and 0.500 mg/g tissue. Reference: Tanaka, E et al., 2016. "Lidocaine concentration in oral tissue by the addition of epinephrine". Anesth. Prg. 63:17-24.

Definitions

The following definition is used in reference to the invention.

As used herein, pre-determined length is a length suitable for the size of the body part being ligated, and is within the know-how of those skilled in the art. Typically, the elastomeric band must be of such structure and elastic nature that when stretched about the neck of the scrotal pouch of an animal and there fastened, it has sufficient elastic constriction force to cause ligation. It must also allow sufficient expansion for passage of the scrotal pouch and contained testicular structure of a large mature animal such as a bovine bull through the orifice defined by the stretched band without breakage. For fastened tubular elastrators, the band must also provide sufficient material to allow fastening in a tensed condition by a deformable metallic fastening clip or similar fastening structure. Normally such a band formed of natural rubber will require a cross-sectional area of approximately 0.1 to 0.4 square inch when the cross-sectional configuration is of a rectangular form. Such a band normally will have a relaxed diameter of from approximately one half to three inches. These parameters may vary generally with the nature of the elastomeric material and particularly for specific purposes while such bands remain operative for castration, and such variant bands are within the ambition and scope of the invention.

The invention claimed is:

1. A ligation band configured for topical control of pain in a livestock animal during bloodless male castration or docking of the livestock animal, the ligation band comprising:
   an elastomeric material in a form of a round band or an elongate round tube for contact with an external body part of the livestock animal, said elastomeric material infused with and coated on its outer surfaces with one or more anesthetics and a skin permeation enhancer or a skin penetration enhancer.

2. The ligation band of claim 1, wherein the ligation band is configured for use with an applicator tool.

3. The ligation band of claim 1, wherein the elastomeric material is sized and shaped for use as a ligature band.

4. The ligation band according to claim 1, wherein the anesthetic is lidocaine and the skin permeation enhancer is isopropyl myristate.

5. The ligation band of claim 4, additionally comprising one or more of meloxicam, bupivacaine, and levobupivacaine.

6. The ligation band according to claim 1, wherein the elastomeric material is one of a natural rubber, a synthetic rubber, a silicone, a polybutadiene, a polyisoprene, a polychloroprene, a nitrile, a poly (styrene-butadiene-styrene) (SBS), a styrene-ethylene-butylene-styrene (SEBS), an ethylene-propylene-diene monomer rubber (EPDM), a polyurethane, and combinations thereof.

7. The ligation band of claim 1, wherein the elastomeric material is additionally infused with and coated on its outer surfaces with one or more antimicrobial agents, one or more antibiotics, one or more anti-inflammatoires, one or more hormones, one or more chemical indicators, one or more vasoconstrictor agents, and combinations thereof.

8. The ligation band according to claim 7, wherein the skin permeation enhancer is one of a fatty acid, a fatty acid ester, a poloxamer, a triglyceride, n-methyl pyrrolidone, terpineol, limonene, dimethyl sulfoxide, and dimethylacetamide.

9. The ligation band according to claim 7, wherein the antimicrobial agent is gentian violet.

10. The ligation band according to claim 7, wherein the anti-inflammatory compound is one or more of flunixin, ketoprofen, diclofenac, ibuprofen, dexamethasone, flumethasone, prednisolone, and prednisone.

11. The ligation band according to claim 7, wherein the hormone is one or more of cortisone, hydrocortisone, trenbolone, testosterone, and estradiol.

12. The ligation band according to claim 7, wherein the vasoconstrictive agent is one or more of epinephrine, pseudoephedrine, phenylephrine, thromboxane, and angiotensin.

13. The ligation band according to claim 7, wherein the chemical indicator is one or more of Nile Red, Oil Red, Sudan Red, Congo Red, cresol red, Coomassie Red, Coomassie Blue, methylene blue, Oil Blue, gentian violet, Azure blue, Malachite green, Eosin dyes, Rhodamine dyes, haematoxylin, phenolphthalein, resazurin, phenol red, methyl red, bromothymol blue, thymol blue, Alizarin yellow, povidone iodine, indigo, turmeric, *Catechu* and Annatto extract.

14. The ligation band of claim 1, wherein the elastomeric material is infused with and coated on its outer surfaces with the one or more anesthetics and the skin permeation enhancer or the skin penetration enhancer by swelling of the ligation band in a volatile organic solvent to infuse the one or more anesthetics and the skin permeation enhancer or the skin penetration enhancer within the elastomeric material, and drying of the ligation band to remove the volatile organic solvent and thereby constrict the elastomeric material and bring a portion of the one or more anesthetics and the skin permeation enhancer or the skin penetration enhancer to the outer surfaces of the elastomeric material.

* * * * *